US012697483B2

(12) United States Patent
Higgins

(10) Patent No.: US 12,697,483 B2
(45) Date of Patent: Aug. 4, 2026

(54) INTRAVASCULAR BLOOD PUMP SYSTEM WITHOUT INCREASED CROSSING PROFILE DUE TO GUIDE WIRE

(71) Applicant: CARDIOVASCULAR SYSTEMS, INC., St. Paul, MN (US)

(72) Inventor: Joseph P. Higgins, Wayzata, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 273 days.

(21) Appl. No.: 18/574,966

(22) PCT Filed: Jun. 27, 2022

(86) PCT No.: PCT/US2022/073184
§ 371 (c)(1),
(2) Date: Dec. 28, 2023

(87) PCT Pub. No.: WO2023/278974
PCT Pub. Date: Jan. 5, 2023

(65) Prior Publication Data
US 2024/0325724 A1 Oct. 3, 2024

Related U.S. Application Data

(60) Provisional application No. 63/215,672, filed on Jun. 28, 2021.

(51) Int. Cl.
| | |
|---|---|
| *A61M 60/865* | (2021.01) |
| *A61M 25/00* | (2006.01) |
| *A61M 25/01* | (2006.01) |
| *A61M 25/09* | (2006.01) |
| *A61M 60/13* | (2021.01) |

(Continued)

(52) U.S. Cl.
CPC ...... *A61M 60/865* (2021.01); *A61M 25/0074* (2013.01); *A61M 25/0127* (2013.01); *A61M 25/09* (2013.01); *A61M 60/13* (2021.01); *A61M 60/17* (2021.01); *A61M 60/237* (2021.01)

(58) Field of Classification Search
CPC ............ A61M 60/865; A61M 25/0074; A61M 25/0127; A61M 25/09; A61M 60/13; A61M 60/17; A61M 60/237; A61M 60/216; A61M 5/142
See application file for complete search history.

(56) References Cited

U.S. PATENT DOCUMENTS 7,022,100 B1    4/2006  Aboul-Hosn et al.
8,888,728 B2   11/2014  Aboul-Hosn et al.
(Continued)

OTHER PUBLICATIONS

International Search Report for copending PCT/US2022/073184, 4 pages, Oct. 7, 2022.

*Primary Examiner* — Paula J Stice
(74) *Attorney, Agent, or Firm* — Kagan Binder, PLLC

(57) ABSTRACT

The present invention provides an intravascular blood pump and guide wire and guide wire catheter, the blood pump configured to enter the vasculature at one access site and guide wire catheter and guide wire at a second access site separated from the first access site. The guide wire catheter, or the guide wire, comprise a magnet near a distal end and the blood pump's distal tip comprising a magnet, wherein the magnets align and connect within the vasculature within the iliac artery for further advancement as a connected assembly.

12 Claims, 7 Drawing Sheets

(51) Int. Cl.
    *A61M 60/17*       (2021.01)
    *A61M 60/237*     (2021.01)

(56)            References Cited

U.S. PATENT DOCUMENTS

| | | | |
|---|---|---|---|
| 9,327,068 | B2 | 5/2016 | Aboul-Hosn et al. |
| 9,545,468 | B2 | 1/2017 | Aboul-Hosn et al. |
| 9,561,314 | B2 | 2/2017 | Aboul-Hosn et al. |
| 9,597,437 | B2 | 3/2017 | Aboul-Hosn et al. |
| 10,226,559 | B2 * | 3/2019 | Schuermann ......... A61M 25/09 |
| 2003/0187322 | A1 | 10/2003 | Siess |
| 2004/0002714 | A1 | 1/2004 | Weiss |
| 2011/0004046 | A1 | 1/2011 | Campbell et al. |
| 2011/0276075 | A1 * | 11/2011 | Fung ................. A61B 18/1815 |
| | | | 606/185 |
| 2012/0041254 | A1 | 2/2012 | Schekel |
| 2018/0055979 | A1 | 3/2018 | Corbett et al. |
| 2020/0030512 | A1 | 1/2020 | Higgins et al. |
| 2020/0222168 | A1 | 7/2020 | Laeseke et al. |
| 2020/0405929 | A1 * | 12/2020 | Tan .................... A61M 60/857 |

* cited by examiner

HEART
VALVE

202'

200

16'

ILIAC ARTERY
BRANCH

18

ILIAC ARTERY
BRANCH

CONVERGENCE
AND CONNECTION
POINT

INTRAVASCULAR BLOOD PUMP SYSTEM WITHOUT INCREASED CROSSING PROFILE DUE TO GUIDE WIRE

CROSS-REFERENCE TO RELATED APPLICATIONS

This application claims priority to International Application No. PCT/US2022/073184, filed Jun. 27, 2022, which in turn claims priority to and the benefit of U.S. Provisional Application Ser. No. 63/215,672, filed Jun. 28, 2021 and entitled INTRAVASCULAR BLOOD PUMP SYSTEM WITHOUT INCREASED CROSSING PROFILE DUE TO GUIDE WIRE, both of which are incorporated herein by reference in their entireties for all purposes.

STATEMENT REGARDING FEDERALLY SPONSORED RESEARCH OR DEVELOPMENT

Not Applicable.

BACKGROUND OF THE INVENTION

Field of the Invention

The invention relates to an intravascular blood pump with integrated isolated conductor(s) and delivery of same to target location.

Description of the Related Art

With reference to FIG. 1, the human heart comprises four chambers and four heart valves that assist in the forward (antegrade) flow of blood through the heart. The chambers include the left atrium, left ventricle, right atrium and right ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood.

Thus, as illustrated, the general blood flow comprises deoxygenated blood returning from the body where it is received by the right atrium via the superior and inferior vena cava and is, in turn, pumped into the right ventricle, a process controlled by the tricuspid valve. The right ventricle functions to pump the deoxygenated blood to the lungs via the pulmonary arteries, where the blood is reoxygenated and returned to the left atrium via the pulmonary veins.

Heart disease is a health problem with a high mortality rate. The use of temporary mechanical blood pump devices are used on an increasingly frequent basis to provide short-term acute support during surgery or as temporary bridging support to help a patient survive a crisis. These temporary blood pumps have developed and evolved over the years to supplement the pumping action of the heart on a short-term basis and supplement blood flow as either left or right ventricular assist devices, with the left ventricular assist device ("LVAD") currently the most commonly used device.

Known temporary LVAD devices generally are delivered percutaneously, e.g., through the femoral artery, to locate or position the LVAD inlet in the patient's left ventricle and the outlet in the patient's ascending aorta with the body of the device disposed across the aortic valve. As the skilled artisan will understand, an incision may be made below the patient's groin to enable access to the patient's femoral artery. The physician may then translate guide wire, followed by a catheter or delivery sheath, through the femoral artery and descending aorta until reaching the ascending aorta. The LVAD with attached rotational drive shaft may then be translated through the delivery catheter or sheath lumen, leaving a proximal end of the drive shaft exposed outside of the patient and coupled with a prime mover such as an electric motor or the equivalent for rotating and controlling the rotational speed of the drive shaft and associated LVAD impeller.

Temporary axial flow blood pumps consist generally of two types: (1) those that are powered by a motor integrated into the device that is connected with the pump's impeller (see U.S. Pat. Nos. 5,147,388 and 5,275,580); and (2) those that are powered by an external motor that provides rotational torque to a drive shaft which is, in turn, connected to the pump's impeller (see U.S. Pat. No. 4,625,712 to Wampler and U.S. Pat. No. 5,112,349 to Summers, each hereby incorporated by reference in their entirety).

Known temporary ventricle assist devices ("VAD"), including LVAD and RVAD (right ventricular assist) devices, whether with integrated motor or an external motor, generally comprise the following elements mounted within a housing, listed in order from the inflow end to the outflow end: an inflow aperture(s); a stationary inducer, also known as a flow straightener; a rotational impeller; and a stationary diffuser and/or outflow structure; and an outflow aperture(s) as shown in the exemplary prior art pump and/or impeller assembly cross sectional and cutaway view of FIG. 2.

In FIG. 2, the known device 2 is oriented with the inflow end (distal end) on the left side of the drawing and the outflow end (proximal) on the right side, so that the incoming blood flow in the ventricle enters the device housing through the inflow aperture(s) (not shown), flows through the defined by the surrounding housing 14, ultimately entering the impeller/pump assembly 4. There, the incoming blood encounters the stationary inducer 6 before being urged forward by the rotating impeller 8. The blood flow may then be modified by a stationary diffuser and exits into the aorta via the housing's outflow aperture(s) 10.

Known VAD or LVAD devices further comprise a delivery configuration and a functional or working configuration, with the delivery configuration having a lower profile or smaller diameter than the functional or working configuration to, inter alia, facilitate atraumatic delivery through a delivery sheath. Stated differently, through various means the housing of the VAD or LVAD, and/or the blades of the impeller, may expand to achieve the functional or working configuration and collapse to achieve the delivery configuration. However, known devices collapse and expand the impeller blades and/or the housing wherein the collapsible and expandable housing surrounds at least a portion of the impeller in order to enable moving between an expanded or working configuration and/or require an integrated motor proximate the impeller. See, e.g., U.S. Pat. Nos. 7,027,875; 7,927,068; 8,992,163.

Known LVAD devices will typically comprise an angled housing to accommodate the aortic arch, the angle or bend generally in the range of 135 degrees.

Known ventricular assist devices (VAD) require a guide-wire aided delivery which adds crossing profile of at least 0.018' or 1 French size increase.

Accordingly, it is highly desirable to provide delivery mechanisms comprising guide wire delivery that does not increase the crossing profile. In addition, it would be desirable to provide an atraumatic crossing of the subject heart valve. Thus, the present invention provides an intravascular blood pump and guide wire and guide wire catheter, the blood pump configured to enter the vasculature at one access site and guide wire catheter and guide wire at a second access site separated from the first access site. The guide wire catheter, or the guide wire, comprise a magnet near a distal end and the blood pump's distal tip comprising a magnet, wherein the magnets align and connect within the vasculature within the iliac artery for further advancement as a connected assembly. In some cases the distal tip is curvilinear as undeformed and in others may be substantially straight as undeformed.

Various embodiments of the present invention address these, inter alia, issues.

The figures and the detailed description which follow more particularly exemplify these and other embodiments of the invention.

DETAILED DESCRIPTION OF THE INVENTION

Generally, various embodiments of the present invention are directed to mechanical assist devices for pumping blood in a patient. Improved temporary LVAD or VAD blood pumps are described herein that are delivered percutaneously and intravascularly.

Figure 3:
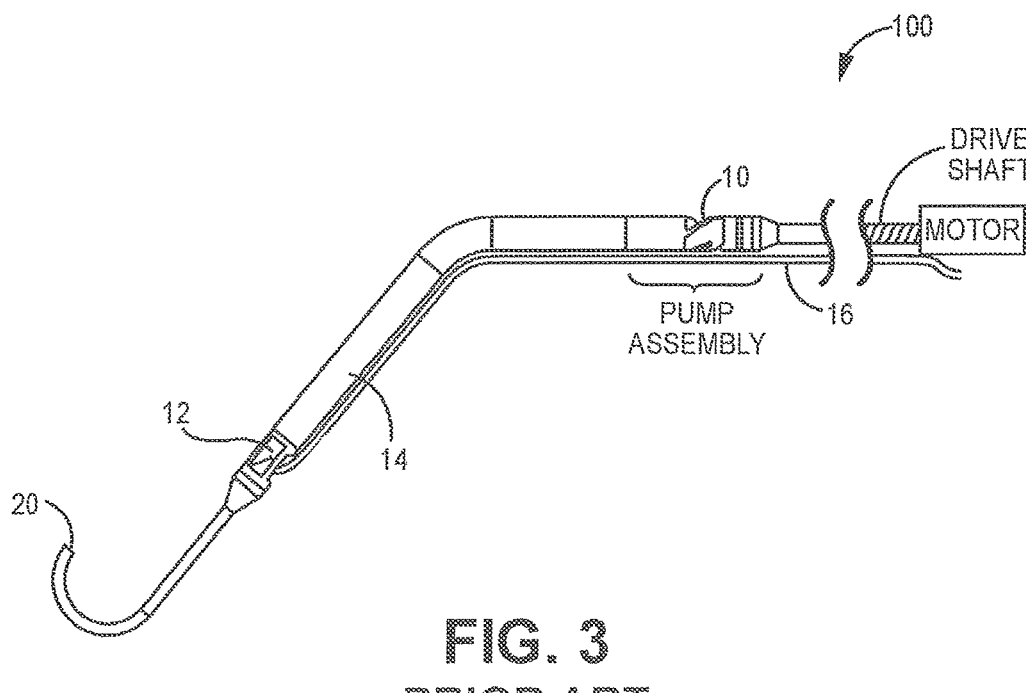
FIG. 3 is a side cutaway view of one embodiment of the present invention.

Referring now to FIG. 3, an exemplary LVAD blood pump 100 is illustrated, with inflow apertures 12 on the left side of the illustration and outflow apertures 10 on the right side of the device. The motor is shown as located on the proximal end of the device outside the patient's body and connected with a rotational drive shaft that is, in turn, connected with the impeller 8 or pump assembly. However, as is well known in the art, the motor may be located within the housing of the device itself, wherein the motor is typically mounted on the proximal side of the the impeller 8 or pump assembly. Either of these configurations may be used together with various embodiments of the present invention as described herein.

The entire length of outer housing 14 is shown as comprising a relatively constant diameter from the inlet or inflow apertures 12 to the outlet or outflow apertures 10. Guide wire 16 is positioned alongside the exterior of the device until reaching the inlet apertures 12 where it enters the lumen of cannula C and extends distally therefrom as shown. Thus, the guide wire 16 does not pass through the impeller 8 or pump assembly. Distal atraumatic tip 20 is shown as a pigtail shape at the distal end of the pump device 102. The configuration shown in FIG. 3 may comprise a delivery configuration with an expandable region (at the pump device 102) compressed within an introducer or delivery sheath or a catheter.

Figure 1:
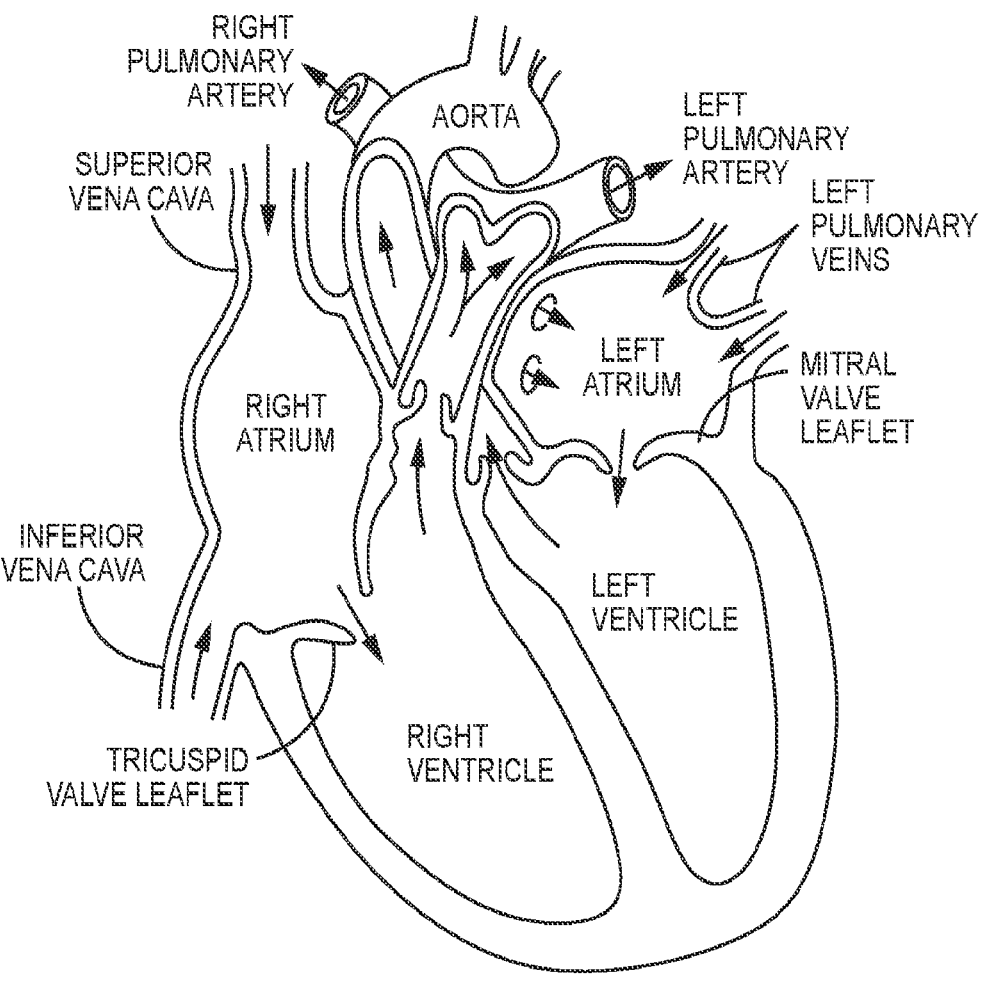
FIG. 1 is a cutaway view of the human heart.
Figure 2:
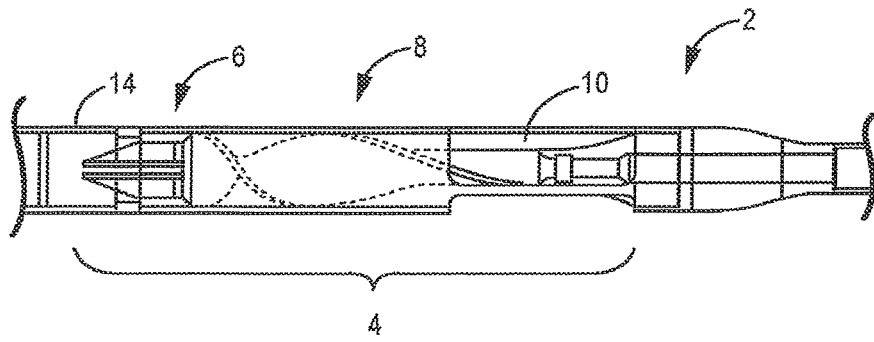
FIG. 2 is a cross-sectional view of a prior art device.

The inventive concepts and embodiments apply generally to the device of FIGS. 2 and 3, but eliminate the guide wire 16 of FIG. 2. Instead, as illustrated in FIGS. 4A-5B, the guide wire 16 or 16' is separately delivered and connects magnetically with the distal end of distal tip 20.

Figure 4A:
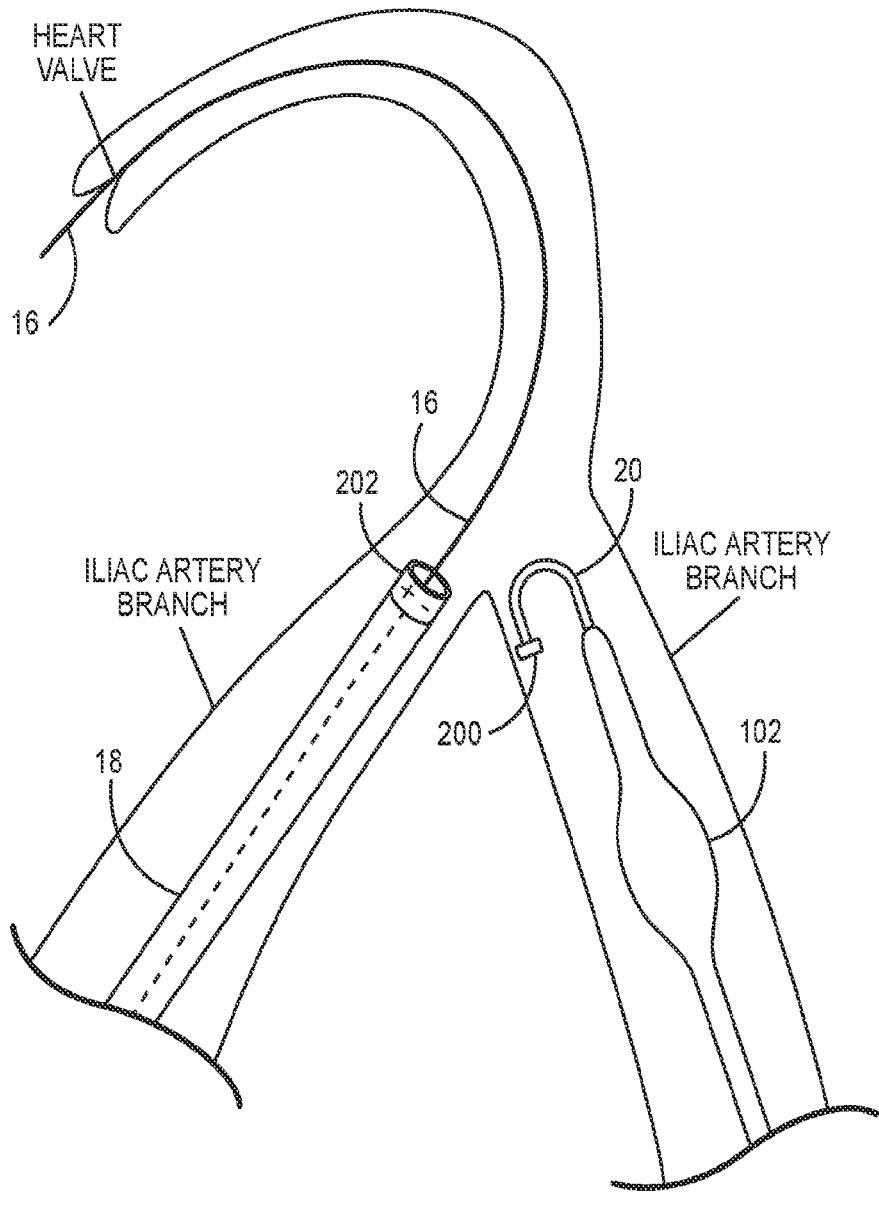
FIG. 4A is a partial cutaway view of one embodiment of the present invention.
Figure 4B:
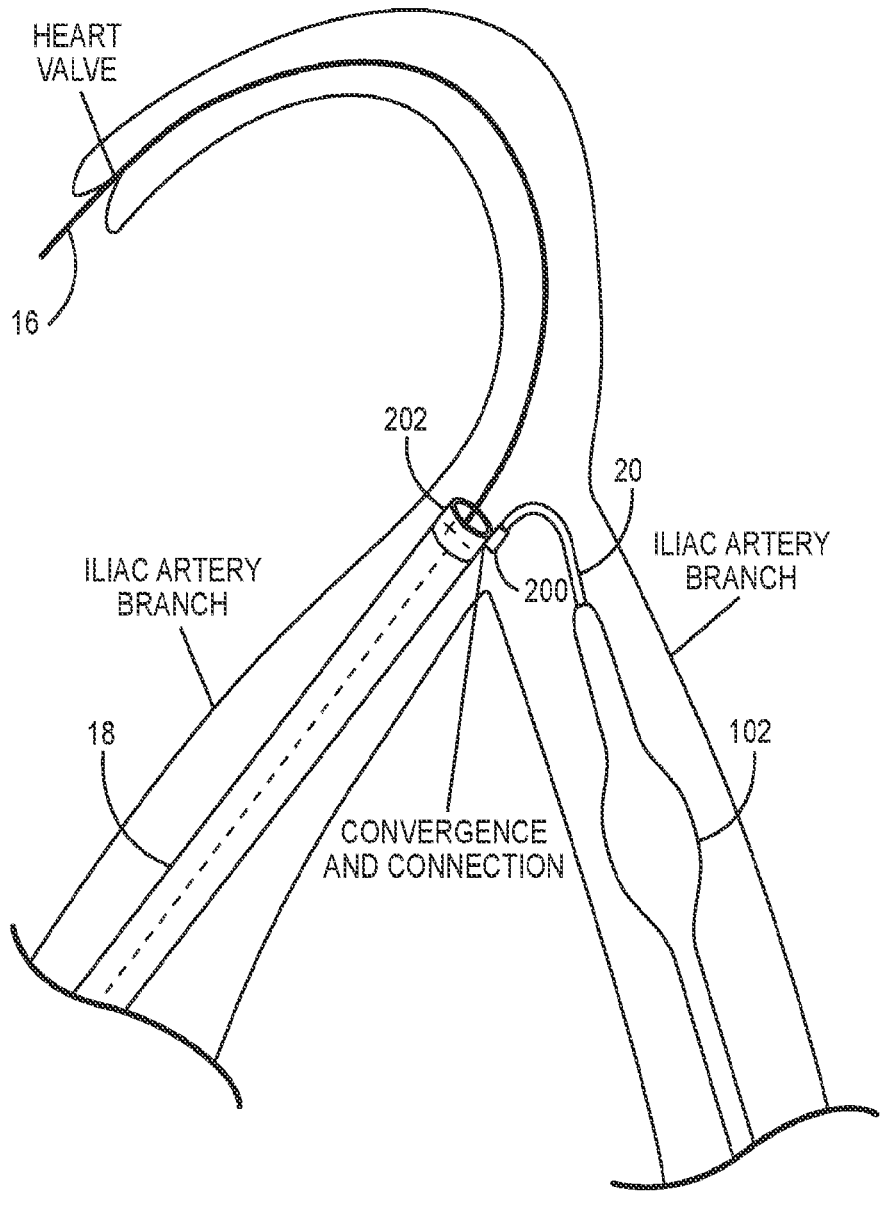
FIG. 4B is a partial cutaway view of one embodiment of the present invention.
Figure 4C:
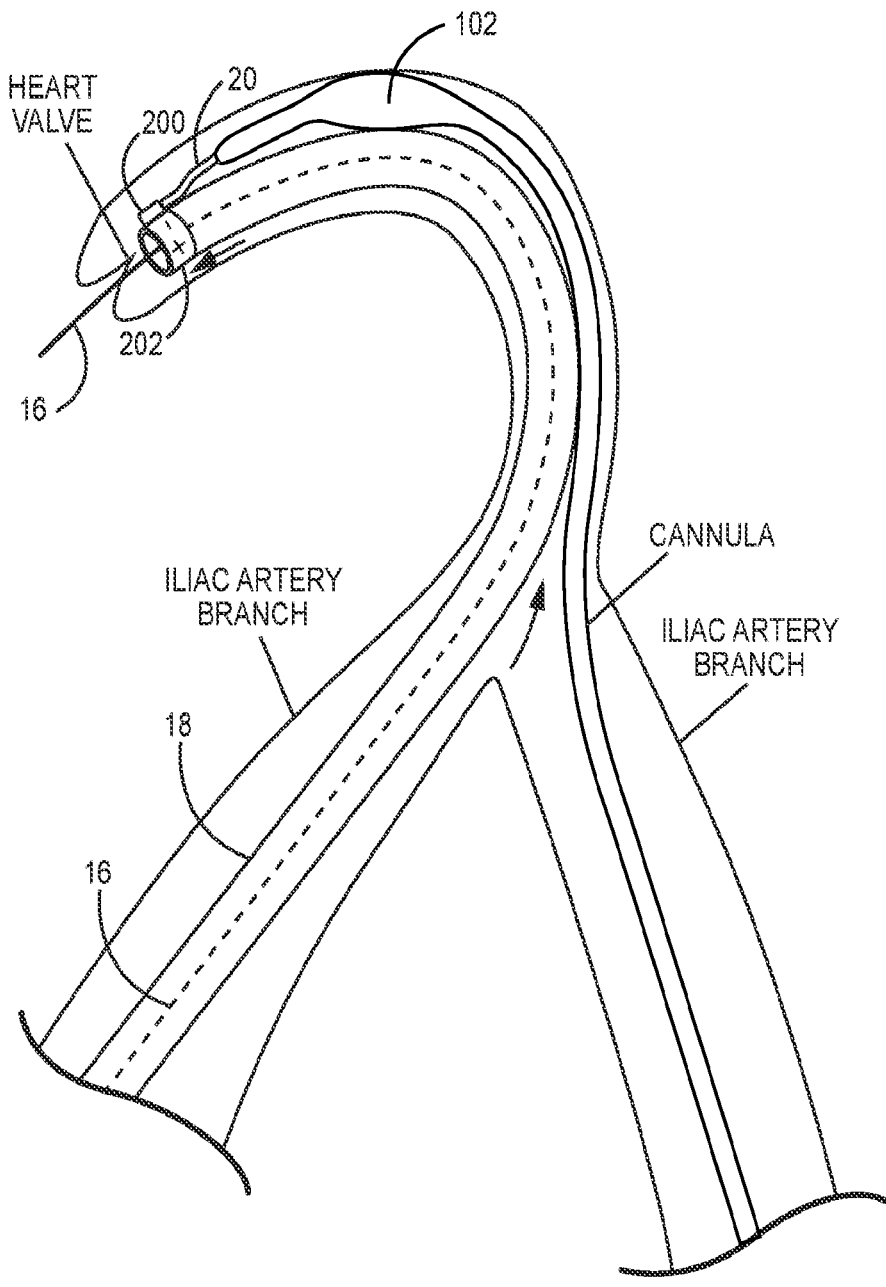
FIG. 4C is a partial cutaway view of one embodiment of the present invention.

Thus, FIGS. 4A-4C illustrates a guide wire catheter 18 configured to position the guide wire 16 at the illustrated location just above the iliac artery branches, wherein a magnet 202 is disposed, mounted, integrated and/or attached to a distal region, preferably the distal end, of the guide wire catheter 18. The guide wire catheter 18 is shown in FIG. 4A with the guide wire 16 therethrough, and with blood pump device 102 being separately introduced the other branch of the iliac artery, wherein the curvilinear distal tip 20 of the blood pump device comprises a magnet 20 at or near its distal end. and the guide wire catheter 18, respectively, converge as shown. At this non-connected alignment stage, the distal tip 20 of device 102 is still in a curved configuration.

FIG. 4B illustrates a convergence and connection between the magnet 202 of the guide wire catheter 18 and the magnet 200 of the distal tip. FIG. 4C illustrates the subsequent advancement of the guide wire catheter 18 over the pre-positioned guide wire 16, which causes the connected distal tip magnet 200 of the blood pump device 102 to translate along the blood vessel as well toward the target within the vessel. Note that the once curvilinear distal tip 20 becomes linear during this translation stage. Once the target is reached by the blood pump device 101, the guide wire catheter magnet 202 is disconnected from the magnet 200 of the distal tip 20 and the guide wire catheter 18 and guide wire 16 may be withdrawn.

Figure 5A:
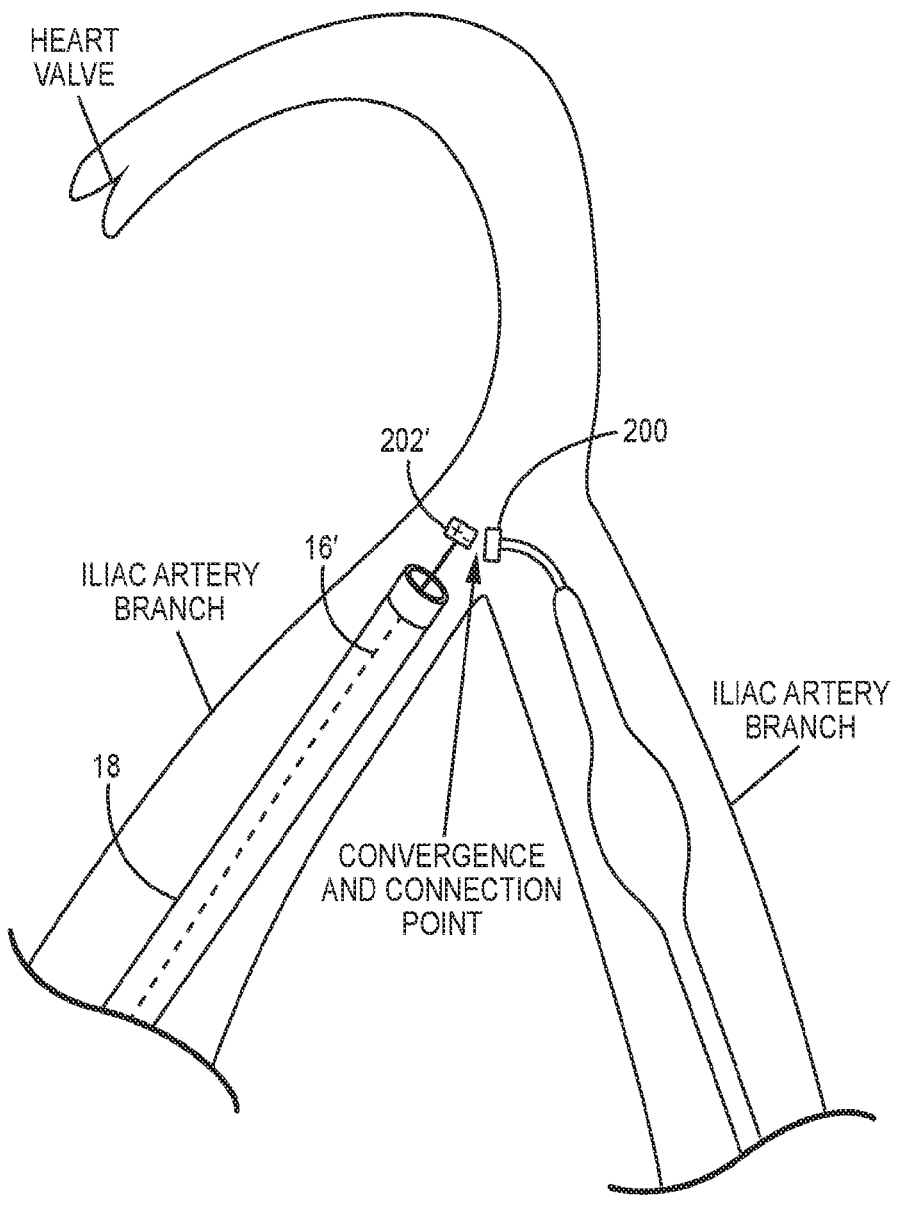
FIG. 5A is a partial cutaway view of one embodiment of the present invention.
Figure 5B:
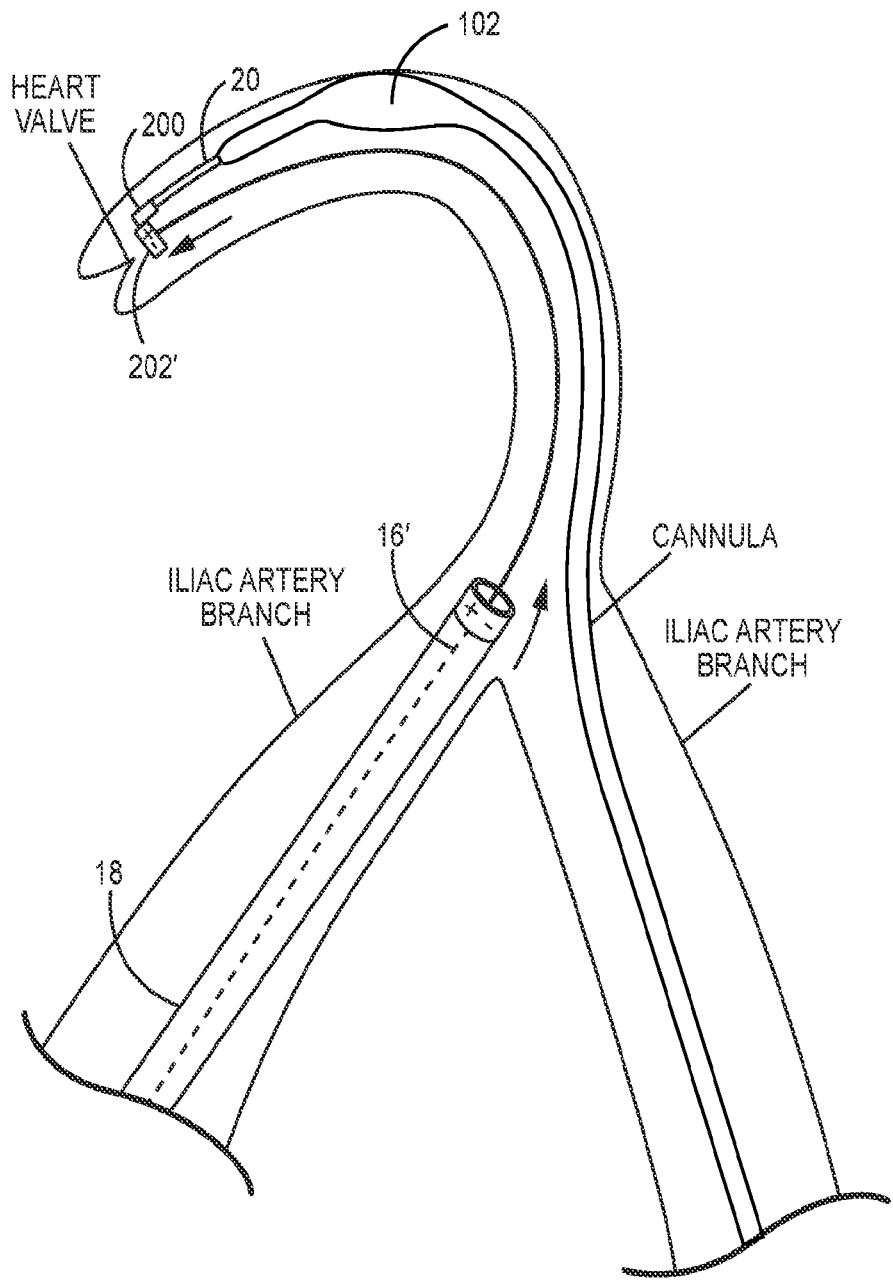
FIG. 5B is a partial cutaway view of one embodiment of the present invention.

FIGS. 5A and 5B illustrate an alternate embodiment wherein the guide wire catheter 18 and guide wire 16' are introduced into one iliac artery branch and the blood pump device 102 is introduced into the other iliac artery branch. Here, a magnet 202' is disposed on or near the distal end of the guide wire 16' as shown, while, as in FIGS. 4A-4C, curvilinear distal tip 20 comprises a magnet 200 as shown. FIG. 5A shows the point at which the guide wire magnet 202' and the curvilinear distal magnet 200 converge and connect. FIG. 5B illustrates the advancement of the guide wire 16', without advancing the guide wire catheter 18 which also advances or translates the connected blood pump device 102 by virtue of the magnetic connection between guide wire magnet 202' and distal tip magnet 200. As in FIG. 4C, advancement in this manner straightens the curvilinear distal tip 20 during translation and positioning at a target. Once the target is reached by the blood pump device 102, the guide wire magnet 202' is disconnected and withdrawn along with the guide wire catheter 18.

As shown in the Figures, the distal tip 20 of device 102 presenting across the valve in a substantially straightened configuration to allow easier and less traumatic crossing of the heart valve. Known devices simply push the curvilinear, e.g., pigtail shaped, distal end across the valve which requires more force and presents risk of trauma to the heart valve. In some embodiments, the distal tip 20 may not be completely straight, but will be deformed in a straightened configuration relative to the undeformed pigtail configuration, thus some curvature will be present in the deformed configuration as the distal tip 20 crosses the valve, but in this deformed configuration, the distal tip of distal end 20 preferably touches the valve leaflets first to facilitate entry and crossing in an atraumatic manner.

The embodiments shown herein comprise a curvilinear distal tip. However, the solutions provided also apply readily to non-curvilinear distal tip devices. In these cases, the alignment and connection steps occur without a straightening of the distal tip as it may already be substantially straightened. The remaining steps proceed as outlined above. Thus, the crossing profile reduction is achieved using any form of distal tip on a blood pump under embodiments of the present invention.

Accordingly, various embodiments may comprise the following:

A blood pump system comprising:

a catheter comprising an impeller assembly comprising a housing and having a flexible distal tip;

a magnet disposed at the distal end of the distal tip;

a guide wire within a guide wire catheter, configured to access the patient's vasculature at a site separated from the impeller assembly, the guide wire catheter or the guide wire, comprising a magnet;

wherein the magnet of the guide wire catheter and the magnet of the flexible distal tip are configured to connect within the patient's vasculature, and wherein the flexible distal tip may be generally straight or may be curvilinear.

If the flexible distal tip is curvilinear in an undeformed configuration, then flexible distal tip may deform to a more straightened profile after connection of the magnets and advancement toward a heart valve.

A delivery method for a ventricular assist blood pump comprising a distal tip, comprising:

providing a guide wire assembly with a magnet disposed near a distal end;

providing a magnet disposed near the distal end of the distal tip of the ventricular assist blood pump;

accessing the patient's vasculature with the guide wire assembly at a first access site into a first blood vessel;

accessing the patient's vasculature with the ventricular assist blood pump at a second access site into a second blood vessel;

advancing the guide wire assembly through the first blood vessel and the ventricular assist blood pump through the second blood vessel to a region of convergence between the first and second blood vessels;

aligning the guide wire assembly magnet and the ventricular assist blood pump magnet within the region of convergence;

creating a magnetically connected assembly comprising at least part of the guide wire assembly and the ventricular assist blood pump;

advancing the magnetically connected assembly;

continuing to advance the magnetically connected assembly across a heart valve to a target location;

disconnecting the magnetically connected assembly and leaving the ventricular assist blood pump at the target location.

In the above delivery method, the flexible distal tip may comprise an undeformed configuration that may be generally straight or that may comprise a generally curvilinear shape. If the undeformed configuration of the flexible distal tip is curvilinear, then advancing the magnetically connected assembly such that the curvilinear distal tip may cause the curvilinear distal tip to deform and at least partially straighten.

The description of the invention and is as set forth herein is illustrative and is not intended to limit the scope of the invention. Features of various embodiments may be combined with other embodiments within the contemplation of this invention. Variations and modifications of the embodiments disclosed herein are possible and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention claimed is:

1. A blood pump system comprising:

a catheter comprising an impeller assembly that includes a housing, the catheter having a flexible distal tip and configured to access a patient's vasculature at a first site:

a magnet disposed at the distal end of the distal tip:

a guide wire extendible within a guide wire catheter, the guide wire catheter configured to access the patient's vasculature at a second site of the patients' vasculature, the guidewire catheter comprising a magnet disposed at or near a distal end of the guide wire catheter:

wherein the magnet of the guide wire catheter and the magnet of the flexible distal tip are configured to connect within the patient's vasculature so that the guide wire catheter impeller assembly can be advanced together along the patient's vasculature to a target location.

2. The blood pump system of claim 1, wherein the flexible distal tip is curvilinear.

3. The blood pump system of claim 2, wherein the curvilinear flexible distal tip deforms to a more straightened profile after connection of the magnets and advancement toward a target in the patient's vasculature.

4. A blood pump system comprising:

a catheter comprising an impeller assembly that includes a housing, the catheter having a flexible distal tip and configured to access a patient's vasculature at a first site:

a magnet disposed at the distal end of the distal tip:

a guide wire extendible within a guide wire catheter, the guide wire catheter configured to access the patient's vasculature at a second site of the patient's vasculature, the guidewire comprising a magnet disposed at or near a distal end of the guide wire:

wherein the magnet of the guide wire and the magnet of the flexible distal tip are configured to connect within the patient's vasculature so that the guide wire catheter impeller assembly can be advanced together along a patient's vasculature to a target location.

5. The blood pump system of claim 4, wherein the flexible distal tip is curvilinear.

6. The blood pump system of claim 5, wherein the curvilinear flexible distal tip deforms to a more straightened profile after connection of the magnets and advancement toward a target in the patient's vasculature.

7. A delivery method for a ventricular assist blood pump comprising a distal tip that includes a first magnet disposed near a distal end of the distal tip, comprising:

providing a guide wire assembly comprising a guide wire catheter and a guide wire, the guide wire assembly further comprising a second magnet disposed at or near a distal end of the guide wire:

accessing a patient's vasculature with the guide wire assembly at a first access site into a first blood vessel:

accessing the patient's vasculature with the ventricular assist blood pump at a second access site into a second blood vessel:

advancing the guide wire assembly through the first blood vessel and the ventricular assist blood pump through the second blood vessel to a region of convergence between the first and second blood vessels:

connecting the first magnet with the second magnet within the region of convergence:

advancing the connected guide wire catheter and ventricular assist blood pump through the patient's vasculature to a target location; and disconnecting the magnetically connected guide wire assembly and leaving the ventricular assist blood pump at the target location.

8. The delivery method of claim 7, wherein the flexible distal dip comprises an undeformed curvilinear shape.

9. The delivery method of claim 7, further comprising advancing the magnetically connected assembly such that the curvilinear distal tip at least partially deforms to at least partially straighten.

10. The delivery method of claim 9, wherein the flexible distal dip comprises an undeformed curvilinear shape.

11. A delivery method for a ventricular assist blood pump comprising a distal tip that includes a first magnet disposed near a distal end of the distal tip, comprising:

providing a guide wire assembly comprising a guide wire catheter and a guide wire, the guide wire assembly further comprising a second magnet disposed at or near a distal end of the guide wire catheter:

accessing a patient's vasculature with the guide wire assembly at a first access site into a first blood vessel:

accessing the patient's vasculature with the ventricular assist blood pump at a second access site into a second blood vessel:

advancing the guide wire assembly through the first blood vessel and the ventricular assist blood pump through the second blood vessel to a region of convergence between the first and second blood vessels:

connecting the first magnet with the second magnet within the region of convergence:

advancing the connected guide wire catheter and ventricular assist blood pump through the patient's vasculature to a target location; and disconnecting the magnetically connected guide wire assembly and leaving the ventricular assist blood pump at the target location.

12. The delivery method of claim 11, further comprising advancing the magnetically connected assembly such that the curvilinear distal tip at least partially deforms to at least partially straighten.

* * * * *